United States Patent
Schmidt

(10) Patent No.: US 10,995,330 B2
(45) Date of Patent: May 4, 2021

(54) METHOD FOR MOBILIZING IMMOBILIZED CELLS

(71) Applicant: LEIBNIZ-INSTITUT FÜR FESTKÖRPER-UND WERKSTOFFFORSCHUNG DRESDEN E.V., Dresden (DE)

(72) Inventor: Oliver G. Schmidt, Dresden (DE)

(73) Assignee: LEIBNIZ-INSTITUT FÜR FESTKÖRPER-UND WERKSTOFFFORSCHUNG DRESDEN E.V., Dresden (DE)

( * ) Notice: Subject to any disclaimer, the term of this patent is extended or adjusted under 35 U.S.C. 154(b) by 214 days.

(21) Appl. No.: 15/115,380

(22) PCT Filed: Jan. 28, 2015

(86) PCT No.: PCT/EP2015/051650
§ 371 (c)(1),
(2) Date: Jul. 29, 2016

(87) PCT Pub. No.: WO2015/113984
PCT Pub. Date: Aug. 6, 2015

(65) Prior Publication Data
US 2017/0166882 A1    Jun. 15, 2017

(30) Foreign Application Priority Data
Jan. 31, 2014 (DE) .......................... 102014201760.2

(51) Int. Cl.
*A61D 19/00* (2006.01)
*A61B 17/425* (2006.01)
*C12N 5/076* (2010.01)
*C12N 11/14* (2006.01)
*C12N 5/071* (2010.01)
*A61K 41/00* (2020.01)

(52) U.S. Cl.
CPC ............ *C12N 11/14* (2013.01); *A61B 17/425* (2013.01); *A61K 41/00* (2013.01); *C12N 5/061* (2013.01); *C12N 5/0612* (2013.01)

(58) Field of Classification Search
CPC ...... C12N 11/14; C12N 5/0612; C12N 5/061; A61B 17/425; A61K 41/00
See application file for complete search history.

(56) References Cited

U.S. PATENT DOCUMENTS

| | | | |
|---|---|---|---|
| 6,695,766 B2 * | 2/2004 | Moruzzi | A61B 17/435 600/34 |
| 9,883,889 B2 * | 2/2018 | Magdanz | C12N 5/0612 |
| 2003/0204128 A1 | 10/2003 | Moruzzi et al. | |
| 2006/0173589 A1 * | 8/2006 | Gusler | B63G 8/08 701/21 |
| 2007/0207186 A1 * | 9/2007 | Scanlon | A61F 2/91 424/424 |
| 2015/0164554 A1 * | 6/2015 | Magdanz | A61D 19/02 600/35 |

FOREIGN PATENT DOCUMENTS

| | | |
|---|---|---|
| DE | 20 2012 212 427 | 1/2014 |
| WO | 2014012801 | 1/2014 |

OTHER PUBLICATIONS

Intrauterine Insemination (IUI) Fertility Centers of New England (Year: 2011).*
Dictionary.com definition of reciprocal (Year: 2005).*
Tottori et al. "Magnetic Helical Micromachines: Fabrication, Controlled Swimming, and Cargo Transport" Adv. Mater. 2012, 24, 811-816. (Year: 2012).*
Kahn et al. "Fallopian tube sperm perfusion (FSP) versus intrauterine insemination (IUI) in the treatment of unexplained infertility: a prospective infertility: a prospective randomized study" Human reproduction vol. 8, No. 6 pp. 890-894. 1993 (Year: 1993).*
Bellastella et al. "Dimensions of human ejaculated spermatozoa in Papanicolaou-stained seminal and swim-up semars uptained from the integrated semen analysis system" Asian Journal of Andrology (2010) 12: 871-879.*
Rémi Dreyfus et al., "Microscopic artificial swimmers", Nature Letters 437, Oct. 6, 2005, pp. 862-865.
Li Zhang et al., "Artificial bacterial flagella: Fabrication and magnetic control", Applied Physics Letters 94, 2009, pp. 1-4.
Veronika Magdanz et al., "Development of a Sperm-Flagella Driven Micro-Bio-Robot", Advanced Materials 25, 2013, pp. 6581-9588.
Shirly Ben-David Makhluf et al., "Loading Magnetic Nanoparticles into Sperm Cells Does Not Affect Their Functionality", Langmuir 22, Nov. 1, 2006, pp. 9480-9482.
Kathrin E. Peyer et al., "Magnetic Helical Micromachines", Chem. Eur. J 19, Mar. 21, 2013, pp. 28-38.

* cited by examiner

Primary Examiner — Blaine Lankford
Assistant Examiner — Lauren K Van Buren
(74) Attorney, Agent, or Firm — Greenblum & Bernstein, P.L.C

(57) ABSTRACT

Method for producing mobility in immobile cells in in vivo or in vitro fertilization. The method includes producing mobility in individual immobile cells that are connected to a microstructure. The microstructure is composed at least partially of magnetic materials and a non-reciprocal movement of the microstructure with the immobile cell is executed by a time-varying, three-dimensional external magnetic field.

16 Claims, No Drawings

METHOD FOR MOBILIZING IMMOBILIZED CELLS

CROSS-REFERENCE TO RELATED APPLICATIONS

The present application is a U.S. National Stage of International Patent Application No. PCT/EP2015/051650 filed Jan. 28, 2015, and claims priority of German Patent Application No. 10 2014 201 760.2 filed Jan. 31, 2014, the disclosures of which are expressly incorporated by reference herein in their entireties.

BACKGROUND OF THE INVENTION

1. Field of the Invention

The invention concerns the fields of microtechnologies, biology and medicine and relates to a method for producing mobility in immobile cells as can be used, for example, for in vivo or in vitro fertilization.

2. Discussion of Background Information

Various methods are known for achieving fertilization both inside and also outside of the body in the case of low mobility of cells, for example spermatozoa, and/or for improving the success rate thereof.

A method is known in which an approximately 200 µm egg cell or a larger embryo is provided with a layer of magnetic particles and, by an application of a magnetic field using a permanent magnet or an electromagnet, the egg cell or embryo is transported into the uterus, where it is stabilized (U.S. Pat. No. 6,695,766 B4). For this purpose, magnetic particles are provided with reactive groups on their surface. The magnetic particles can have a diameter of 0.1 µm to 200 µm. These magnetic particles are brought together with the egg cell or embryo so that the reactive groups of the magnetic particles can react with the reactive groups on the surface of the egg cell or embryo.

Furthermore, according to DE 10 2012 212 427 A1, a method for the controlled movement of motile cells in liquid or gaseous media is known in which motile cells are inserted into or attached to a magnetic particle and, by applying an external magnetic field, the magnetic particles are moved with the motile cells in a directed manner.

Furthermore, methods are known with which artificial helical structures and flexible flagella structures on a micrometer scale can be produced which can be moved and steered in liquids via an external magnetic field (R. Dreyfus, J. Baudry, M. L. Roper, M. Fermigier, H. A. Stone and J. Bibette, Nature, 2005, 437, 862-865; L. Zhang, J. J. Abbott, L. Dong, B. E. Kratochvil, D. Bell and B. J. Nelson, Appl. Phys. Lett., 2009, 94, 064107).

The known methods have the disadvantage that they do not allow individual immobile cells on a micrometer scale to be moved and guided inside the body of a mammal or a human using a magnetic field. Additionally, with the methods cited, the magnetic particles always remain inside the body of a mammal or human.

SUMMARY OF THE EMBODIMENTS

The object of the present invention is to specify a method for producing mobility in individual immobile cells, with which method activity and guided mobility in previously immobile cells is achieved.

The object is attained by the invention disclosed in the claims. Advantageous embodiments are the subject matter of the dependent claims.

In the method according to the invention for producing mobility in immobile cells, an immobile cell is connected to a microstructure, wherein the microstructure is composed at least partially of magnetic materials and a non-reciprocal movement of the microstructure with the immobile cell is executed by means of a time-varying, three-dimensional external magnetic field.

Immobile, non-motile sperm cells are advantageously used as immobile cells.

Likewise advantageously, a microstructure composed of a magnetic material or a material having magnetic particles is used.

Also advantageously, ferromagnetic or paramagnetic material is used as magnetic material.

It is also advantageous if iron, iron oxide, cobalt or nickel or alloys of these materials, or these materials in combination with other materials, are used as magnetic material and if non-magnetic materials coated with magnetic materials are used.

It is likewise advantageous if a microstructure composed of a polymer is used, which polymer contains magnetic particles or which is coated fully or partially with magnetic particles or materials.

And it is also advantageous if a microstructure is used which has the shape of a helical structure or of an artificial flexible flagellum.

It is furthermore advantageous if the positive-fit connection of the microstructure to the immobile cell is achieved by the shape of the microstructure.

It is also advantageous if the connection of the microstructure to the immobile cell is achieved by means of a biochemical functionalization of surfaces.

And it is also advantageous if the microstructure used has lengths of 1 µm-200 µm and diameters of 1 µm to 20 µm.

It is likewise advantageous if the connection of the immobile cell and microstructure is performed in vitro.

And it is also advantageous if a time-varying, three-dimensional magnetic field is achieved using permanent magnets or electromagnets.

According to the invention, the movable cells produced according to the invention are used inside the body of a mammal or human.

Advantageously, the controlled movement of originally non-motile sperm cells takes place in the uterus, through the fallopian tube to the egg cell, where successful fertilization occurs.

DETAILED DESCRIPTION OF THE EMBODIMENTS

With the method according to the invention for producing mobility in individual immobile cells, it is for the first time possible to achieve activity and guided mobility in previously immobile cells.

This is achieved by connecting the immobile cell to a microstructure that provides the driving force. The connection occurs either in a positive fit through a mechanical coupling of the microstructure to the cell or alternatively through a biochemical coupling by means of functionalized surfaces of the cell and of the respective microstructure. Advantageously, in a positive-fit connection, the microstructure comprises a ring-like opening, the dimensions of which are matched to the size of the immobile cell or are embodied only slightly smaller or larger. The dimensions of the immobile cells and of the microstructures are thereby on the micrometer scale. The microstructures advantageously have lengths of 1 μm-200 μm and their diameters correspond roughly to the size of an individual cell. The connection between the immobile cell and microstructure allows on the one hand the movement of immobile cells together with the microstructure and on the other hand also ensures a releasable connection, so that the microstructure can, if necessary, also be released after transport of the immobile cell to the desired location and removed from said location again in a directed manner.

The directed movement of the immobile cells with the microstructure is on the one hand achieved through the use of magnetic materials of which the microstructure is fully or partially composed, and on the other hand through the application of a time-varying, three-dimensional external magnetic field, as a result of which the microstructure executes a non-reciprocal or non-time-reversible movement together with the cell.

Advantageously iron, iron oxide, cobalt or nickel or alloys of these materials, or these materials in combination with other materials, can be used as magnetic materials. In the event that the produced microstructure itself does not have magnetic properties or has insufficient magnetic properties, it is enclosed fully or partially by magnetic materials.

A partial or full enclosure of the microstructure with a biocompatible protective layer is also possible.

Advantageously, polymer materials can also be used as microstructure material, wherein the polymers can contain magnetic materials or are coated fully or partially therewith.

With the solution according to the invention, it is for the first time possible to make immobile cells movable and to steer the movement thereof in a desired direction inside the body of a human or an animal.

Within the scope of this invention, immobile cells are to be understood as meaning living cells which do not have the ability to move autonomously in liquid media.

Once the immobile cell is connected to the microstructure, a time-varying external magnetic field is applied. By altering this magnetic field, a torque is exerted on the specially shaped microstructure and thus a non-reciprocal movement of the cell microstructure is produced, which causes a forward movement. The direction of movement of the microstructure with the cell can also be controlled by an external magnetic field. A time-varying, three-dimensional external magnetic field of this type can be produced by a moving permanent magnet or preferably by a three-dimensional arrangement of electromagnets.

The shape of the microstructure is of particular importance. Advantageously, a helical structure or an artificial flexible flagellum is thereby used as a shape. By means of a time-varying external magnetic field, the helical structure is set in a rotational motion and is thereby moved in a forward direction. Advantageously, the diameter of the helical structure is matched to the diameter of the cell. However, the microstructure can also be a flagellum structure that is attached to the immobile cell. The flagellum is set in a wriggling motion by a time-varying, three-dimensional external magnetic field, whereby a movement of the immobile cells is achieved.

According to the invention, by means of the attachment of the microstructure to an immobile cell, an artificial flagellum is effectively achieved to produce movement in the case of an immobile sperm cell.

Particularly advantageously, the method according to the invention can be applied to assist with natural in vivo fertilization where spermatozoa exhibit highly reduced mobility or no longer have any mobility at all. In this manner, an increased success rate for fertilizations is achieved, and an alternative reproduction technique is made available, since a removal of the egg cell from the animal body or human body is not necessary. The sperm cells connected to the microstructure can be introduced directly into the uterus. Through the application of a time-varying magnetic field, the sperm cell is thus moved through the fallopian tube to the egg cell in a targeted manner, and fertilization occurs.

As a result of the special coupling of the microstructure, the microstructure can also be removed from the immobile cell, for example in the case of a helical structure by reversing the rotational direction of the magnetic field and thus also reversing the rotation of the microstructure. The microstructure can thus be completely removed from the animal body or human body.

However, the method according to the invention can also be used for in vitro fertilization by transporting the cells to the egg cell outside of the body.

Specifically, the advantage of the solution according to the invention is that cells which were originally non-motile can be moved inside an animal body or human body, and that the magnetic materials do not need to remain inside the body and therefore do not have any negative effects on the organism.

The invention is explained below in greater detail with the aid of an exemplary embodiment.

EXAMPLE

A biocompatible polymeric helical structure composed of OrmoComp® (micro resist technology GmbH) is produced by means of three-dimensional laser writing. The helical structure has a diameter that is slightly smaller than the width of a human sperm head, that is, approximately 3 μm, and a length of 80 μm. The helical structure is then coated with a thin iron layer having a thickness of 30 nm in a vapor deposition process. The helical structure is designed to be ring-shaped at one end. The ferromagnetic helical structure is moved by means of a time-varying external magnetic field and mechanically coupled to a non-motile sperm. This takes place outside of the human body, that is, in vitro. Following the mechanical coupling, the non-motile natural sperm flagellum is located in the middle of the helical structure. One or more spermatozoa coupled to helical structures are subsequently injected into the uterus of the female body via insemination. The spermatozoa coupled to helical structures are then set in motion by a rotating external magnetic field, steered through the fallopian tube and ultimately brought into contact with the egg cell, where successful fertilization takes place. The rotational direction of the magnetic field is then reversed, which causes the helical structure to move in the opposite direction and to therefore be separated and decoupled from the sperm. Finally, the helical structure is moved out of the body of the female.

The invention claimed is:

1. A method for producing mobility for an immobilized sperm cell comprising attaching a sperm to a ring-like opening of a microstructure made of magnetic material comprising a helical structure or an artificial flexible flagellum, executing a non-reciprocal movement of the helical structure or flagellum attached to the microstructure using a three dimensional external magnetic field, moving the microstructure to a desired location, and releasing the immobilized sperm cell.

2. The method according to claim 1, wherein the magnetic material comprises magnetic particles.

3. The method according to claim 1, wherein the magnetic material comprises ferromagnetic or paramagnetic material.

4. The method according to claim 1, wherein the magnetic material comprises iron, iron oxide, cobalt, nickel, or alloys of these materials.

5. The method according to claim 4, wherein the magnetic material is provided as coating on a non-magnetic material.

6. The method according to claim 1, wherein the microstructure comprises a polymer which contains magnetic particles, is fully coated by magnetic particles, or is partially coated with magnetic particles.

7. The method according to claim 1, wherein the microstructure has a helical structure.

8. The method according to claim 7, wherein a diameter of the helical structure corresponds to a diameter of the immobilized sperm to be connected.

9. The method according to claim 7, wherein a diameter of the helical structure is smaller than a width of a human sperm head.

10. The method according to claim 1, wherein a positive fit connection between the microstructure and the immobilized sperm cell is achieved by a biochemical functionalization of surfaces.

11. The method according to claim 1, wherein the microstructure has a length of 1-200 microns and a diameter of 1 to 20 microns.

12. The method according to claim 1, wherein the connection between the microstructure and the immobilized sperm cell is produced in vitro.

13. The method according to claim 1, wherein the three dimensional magnetic field is produced by permanent magnets or electromagnets.

14. The method according to claim 1, wherein the method further comprises fertilizing an egg cell by moving the immobilized sperm cell in a uterus and through the fallopian tube to the egg cell.

15. The method according to claim 1, wherein the helical structure is composed of polymer material that is coated with magnetic particles.

16. The method according to claim 15, wherein the polymer material is coated with magnetic particles by a vapor deposition process.

* * * * *